US006187743B1

(12) United States Patent
Obi-Tabot (10) Patent No.: US 6,187,743 B1
(45) Date of Patent: *Feb. 13, 2001

(54) COMPOSITION AND METHOD FOR ENHANCING WOUND HEALING

(75) Inventor: Eliot T. Obi-Tabot, Framingham, MA (US)

(73) Assignee: Deroyal Industries, Inc., Powell, TN (US)

(*) Notice: Under 35 U.S.C. 154(b), the term of this patent shall be extended for 0 days.

This patent is subject to a terminal disclaimer.

(21) Appl. No.: 09/459,753

(22) Filed: Dec. 10, 1999

Related U.S. Application Data

(63) Continuation of application No. 09/358,777, filed on Jul. 22, 1999, now Pat. No. 6,046,160.

(51) Int. Cl.[7] .................. A61K 38/00; A61K 31/355; A61K 31/34

(52) U.S. Cl. .................. 514/2; 514/458; 514/474

(58) Field of Search ................ 514/2, 458, 474

(56) References Cited

U.S. PATENT DOCUMENTS

| | | | |
|---|---|---|---|
| 4,837,024 | * 6/1989 | Michaeli | 424/446 |
| 4,841,962 | * 6/1989 | Berg et al. | 128/156 |
| 4,950,688 | * 8/1990 | Bowser et al. | 514/847 |
| 5,133,965 | * 7/1992 | Fountain | 424/446 |
| 5,196,196 | * 3/1993 | Scott et al. | 424/94.64 |
| 5,633,284 | * 5/1997 | Meyer | 514/178 |
| 5,633,285 | * 5/1997 | Martin | 514/724 |
| 5,658,956 | * 8/1997 | Martin et al. | 514/724 |
| 5,658,957 | * 8/1997 | Martin | 514/724 |
| 5,676,967 | * 10/1997 | Williams et al. | 424/443 |
| 5,693,624 | * 12/1997 | Hardy et al. | 514/54 |
| 5,723,144 | * 3/1998 | Hardy | 424/445 |
| 5,800,372 | * 9/1998 | Bell et al. | 602/48 |
| 5,834,008 | * 11/1998 | Greenspan et al. | 424/443 |
| 5,853,749 | * 12/1998 | Hobbs | 424/443 |
| 5,874,479 | * 2/1999 | Martin | 514/724 |
| 6,046,160 | * 4/2000 | Obi-Tabot | 514/2 |

FOREIGN PATENT DOCUMENTS

138385 * 4/1985 (EP).

OTHER PUBLICATIONS

Burton et al., "Collagen Sponge for Leg Ulcers," *British Journal of Dermatology* vol. 99 (1978), 681–5.
Ellis et al., "Recent Advances in Tissue Synthesis in Vivo by Use of Collagen–Glycosaminoglycan Copolymers," *Biomaterials* vol. 17, No. 3 (1996), 291–9.
Hait et al., "Microcrystalline Collagen as a Biologic Dressing, Vascular Prosthesis, and Hemostatic Agent," *Surgical Forum*, 51–3(No date available).
Hansbrough et al., "Burn Wound Closure with Cultured Autologous Keratinocytes and Fibroblasts Attached to a Collagen –Glycosaminoglycan Substrate," *Journal of the American Medical Association* vol. 262, No. 15 (Oct. 20, 1989), 2125–30.
Kolenik et al., "Use of a Lyophilized Bovine Collagen Matrix in Postoperative Wound Healing," *Dermatol Surg* vol. 25 (1999), 303–7.
Mathews et al., *Biochemistry*, 2nd ed., 742–3.No date available.
Mian et al., "Lyophilized Type–I Collagen and Chronic Leg Ulcers," *Int. J. Tiss. Reac.* vol. 13, No. 5 (1991), 257–69.
Mutter et al., "Biomaterial Supports for Colonic Wall Defect Healing," *Biomaterials* vol. 17, No. 14 (1996), 1411–5.
Rasmussen et al., "Collagen Types I and III Propeptides as Markers of Healing in Chronic Leg Ulcers," *Ann. Surg.* vol. 216, No. 6 (Dec. 1992), 684–91.
Tuan et al., "In Vitro Fibroplasia: Matrix Contraction, Cell Growth, and Collagen Production of Fibroblasts Cultured in Fibrin Gels," *Experimental Cell Research* vol. 223 (1996), 127–34.
Adelmann–Grill et al., "Immunological Safety Evaluation of a Haemostatic Agent and Wound Dressing Made of Horse Collagen Fibrils," *Arzneim.–Forsch./Drug Res.* vol. 37 (II), No. 7 (1987), 802–5.
Elson, "Injectable Collagen and Autoimmune Disease," *J Dermatol Surg Oncol* vol. 19 (1993), 165–8.
McCoy et al., "Characterization of the Humoral Immune Response to Bovine Collagen Implants," *Arch Dermatol* vol. 121 (Aug. 1985), 990–4.
McCoy et al., "Connective Tissue Diseases and Bovine Collagen Implants," *Journal of the American Academy of Dermatology* vol. 16 (1987), 315–8.
Rosen et al., "Use of Gelatin Matrix Implant in Patients Hypersensitive to Bovine Collagen," *Journal of the American Academy of Dermatology* vol. 22, No. 5, Part 1 (May 1990), 848–9.

(List continued on next page.)

*Primary Examiner*—Raymond Henley, III
(74) *Attorney, Agent, or Firm*—Chapman and Cutler (57) ABSTRACT

The healing of wounds is enhanced by contacting the wound surfaces with a dressing of D-glucose polysaccharide obtained by hydrolysis of starch containing ascorbic acid, collagen type I and alpha-tocopherol acetate. The collagen type I, and the ascorbic acid in the dressing are the typical chemotactic agents of neutrophils, fibroblasts and/or endothelial cells. These combinations can be present in the dressing as a gel. The composition material can be applied to the wound as a particulate material such as a powder, or as material such as a gel, paste, dispersion, solution or syrup. Wounds, in particular those occurring in the skin as second and third degree burns, stasis ulcers, trophic lesions, such as decubitus ulcers, severe cuts and abrasions which are commonly resistant to the natural healing process, may be treated with this composition. The application of this combination to open wounds greatly accelerates the rate of healing and reduces scarring. The invention includes an article useful in the therapy for surface wounds comprising the suspension of particles on non-adherent gauze and a bandage tape.

38 Claims, 4 Drawing Sheets

OTHER PUBLICATIONS

Ames et al., "Oxidants Are a Major Contributor to Aging," *Annals New York Academy of Sciences*, 85–95. (No date available).

Burton et al., "Vitamin E as an in Vitro and in Vivo Antioxidant," *Annals New York Academy of Sciences*, 7–22. (No date available).

Ette et al., "Vitamins and Trace Elements Profiles in Chronic Leg Ulcers in Nigerians," *Tropical and Geographical Medicine* vol. 34 (1982), 73–5.

Grant, letter to the editor, *Canadian Medical Association Journal* vol. 126 (May. 15, 1982), 1153.

Maderazo et al., "Additional Evidence of Autooxidation as a Possible Mechanism of Neutrophil Locomotory Dysfunction in Blunt Trauma," *Critical Care Medicine* vol. 18, No. 2 (Feb. 1990), 141–7.

Maderazo et al., "A Randomized Trial of Replacement Antioxidant Vitamin Therapy for Neutrophil Locomotory Dysfunction in Blunt Trauma," *The Journal of Trauma* vol. 31, No. 8 (Aug. 1991), 1142–50.

Martin, "The Use of Antioxidants in Healing," *Dermatol Surg* vol. 22 (1996), 156–60.

Niki, "Interaction of Ascorbate and α–Tocopherol," *Annals New York Academy of Sciences*, 186–99. (No date available).

Packer et al., "Vitamin E: Introduction to Biochemistry and Health Benefits," *Annals New York Academy of Sciences*, 1–6. (No date available).

Ramasastry et al., "Biochemical Evidence of Lipoperoxidation in Venous Stasis Ulcer," *Annals New York Academy of Sciences*, 506–8. (No date available).

Rock et al., "Carotenoids and Antioxidant Nutrients Following Burn Injury," *Annals New York Academy of Sciences*, 274–6. (No date available).

Stryer, *Biochemistry*, 4th ed., 454–5. (No date available).

Baumann et al., "The Effects of Topical Vitamin E on the Cosmetic Appearance of Scars," *Dermatol Surg* vol. 25 (1999), 311–5.

Brodkin et al., "Sensitivity to Topically Applied Vitamin E," *Arch Derm* vol. 92 (Jul. 1965), 76–7.

de Groot et al., "Allergic Contact Dermatitis from Tocopheryl Acetate in Cosmetic Creams," *Contact Dermatitis* Vo. 25 (1991), 302–4.

Ehrlich et al., "Inhibitory Effects of Vitamin E on Collagen Synthesis and Wound Repair," *Ann. Surg.* vol. 175, No. 2 (Feb. 1972), 235–40.

Havlik et al., "Vitamin E and Wound Healing," *Plastic and Reconstructive Surgery*, (Dec. 1997), 1901–2.

Perrenoud et al., "An Epidemic Outbreak of Papular and Follicular Contact Dermatitis to Tocopheryl Linoleate in Cosmetics," *Dermatology* vol. 189 (1994), 225–33.

\* cited by examiner

1- CONTROL (SALINE)
2- 50mg/cm² MALTODEXTRIN (Containing Ascorbic Acid)
3- 50 mg/cm² MALTODEXTRIN + 2µg/cm² COLLAGEN
4- 50 mg/cm² MALTODEXTRIN + 10µg/ml/cm² TOCOPHEROL
5- 50 mg/cm² MALTODEX + 2µg/cm² COLLAG + 10µg/ml/cm² TOCOPH

COMPOSITION AND METHOD FOR ENHANCING WOUND HEALING

This application is a continuation of a prior U.S. patent application Ser. No. 09/358,777, filed Jul. 22, 1999, now U.S. Pat. No. 6,046,160.

BACKGROUND OF THE INVENTION

1. Field of the Invention

This invention relates to medicinal dressings that provide an advanced healing environment for wounds. Good wound healing is characterized by rapid and complete regeneration of the damaged tissue. Considerable efforts have been expended in the study of wound dressings with the aims of finding which dressings are most effective in promoting wound healing. The process of wound healing is complex and is not fully understood. High macrophage activity is desirable, particularly during the early stages of healing, to kill bacteria and to remove cell debris and foreign matter. This activity is generally accompanied by inflammation. High fibroblast activity is desirable, particularly during the later stages of healing, to produce a high rate of regeneration.

Enhanced concentrations of active free radicals are often found in wounds, in particular small oxygen-containing free radicals such as the hydroxyl radical (OH.), the hydroperoxyl radical (OOH.) and the superoxide anion ($O_2^-$). The latter two are in protonation equilibrium, with the anion predominating at physiological pH; the hydroperoxyl radical is a more active free radical than the superoxide anion. The presence of these radicals is believed to be advantageous in the early stages of healing, attracting macrophages into the wound and promoting the respiratory burst. Their continued presence is, however, believed to be detrimental. They are thought to promote continued inflammation and so to delay healing and in severe cases to induce tissue necrosis and permanent tissue damage. In contrast, oxidizing species without unpaired electrons, such as hydrogen peroxide ($H_2O_2$), are believed to be considerably less harmful.

2. Description of the Related Art

The process of wound healing consists of three phases during which the injured tissue is repaired, regenerated, and new tissue is reorganized into a scar. These three phases are classified as: a) an inflammation phase which begins from day 0 to 3 days, b) a cellular proliferation phase from 3 to 12 days, and c) a remodeling phase from 3 days to about 6 months. In all three phases, antioxidants play a vital role in the healing process.

In the inflammation phase, inflammatory cells, mostly neutrophils, enter the site of the wound followed by lymphocytes, monocytes, and later macrophages. The neutrophils that are stimulated begin to release proteases and reactive oxygen species into the surrounding medium with potential adverse effects on both the adjacent tissues and the invading microorganisms. The oxygen species known to be released by the neutrophils are superoxide ($O_2^-$) through the action of a plasma membrane-bound NADPH oxidase, hydrogen peroxide ($H_2O_2$) formed by action of dismutation of $O_2^-$, and HOCl produced by the action of myeloperoxidase with $H_2O_2$.

The proliferative phase consists of laying down new granulation tissue, and the formation of new blood vessels in the injured area. The fibroblasts, endothelial cells, and epithelial cells migrate in the wound site. These fibroblasts produce the collagen that is necessary for wound repair. Ascorbic acid is crucial in the formation of collagen. Several studies have demonstrated that ascorbic acid was capable of overcoming the reduced proliferative capacity of elderly dermal fibroblasts, as well as increasing collagen synthesis in elderly cells by similar degrees as in newborn cells even though the basal levels of collagen synthesis are age dependent A decrease of ascorbic acid at the injury area will decrease the rate of wound healing.

In reepithelialization, epithelial cells migrate from the free edges of the tissue across the wound. This event is succeeded by the proliferation of epithelial cells at the periphery of the wound. Research has also shown that reepithelialization is enhanced by the presence of occlusive wound dressings which maintain a moisture barrer.

The final phase of wound healing, which is remodeling, is effected by both the replacement of granulation tissue with collagen and elastin fibers and the devascularization of the granulation tissue. Recent studies have shown that topical application of antioxidants, especially alpha-tocopherol, reduces scarring and normalizes blood coagulation during therapy.

As described in U.S. Pat. No. 3,812,252, a particularly effective healing treatment for wounds and skin defects such as burns, ulcers and lesions is the application of a medicinal dressing containing as an essential ingredient starch hydrolysate having Dextrose Equivalent of less than about 35. In such wound treatment the starch hydrolysate produces the formation of a film which is intimately adhered to the underlying granulation tissue and which is semi-permeable to gas and fluids and provides an ideal protective cover that will reduce fluid and plasma losses and invasion by pathogenic bacteria. In addition, it appears that the starch hydrolysate provides a topical or local hyperalimentation, that is local nutrition, providing a gradual release of glucose which is particularly effective in nutrition of tissue, both damaged and nascent, which have become relatively isolated from normal blood flow nutrition. The cessation of blood flow to such an ischemic lesion can be developed in a slow and gradual form such as in the case of decubitus ulcers and stasis ulcers, or may take place more acutely such as in thermo-radiation and chemical burns. In the absence of nutrition, the rate of fluid delivery of nutrients decreases bringing a progressive impairment in the viability of cells and tissues. This eventually leads to degeneration and death of the tissue and cells in a condition known as necrosis. Necrosis is generally accompanied by bacterial, fungal and/or viral contamination. As further pointed out in the aforementioned patent, treatment of exudative skin wounds with a starch hydrolysate dressing produces a greatly reduced bacteria count of an infected wound and inhibits infection of an uninfected wound. In addition, application of the starch hydrolysate to a wound or ulcer produces a film or semi-permeable membrane which allows edematous liquid to pass through while proteinaceous material is retained within the body, allowing reduction in the volume of exudate in relatively clean condition.

U.S. Pat. No. 4,837,024 describes compositions which enhance and promote the wound healing process and which comprise suspensions of the fibrous protein, collagen, and of a polysaccharide, namely a glycosaminoglycan. The glycosaminoglycan is one which exhibits chemotaxis for fibroblasts or endothelial cells; the preferred glycosaminoglycans are said to be heparin, heparan sulfate and alginate, although it should be noted that alginate is not in fact a glycosaminoglycan.

The compositions of the present invention include collagen type I, vitamins such as ascorbic acid (vitamin C) and alpha-tocopherol (vitamin E), and particulate starch hydrolysate that are applied on wounds to promote the formation and growth of healthy granulation tissue. The repair process for even minor breaches or ruptures takes a period of time extending from hours and days to weeks; and in some instances, as in ulceration, the breach or rupture may persist for extended periods of time, i.e., months or even years. At all times, be it brief or extended, the potential for invasion by pathogenic organisms or foreign substances continues until new tissue has been generated to fully close the rupture or breach. Because of the danger of infections, the customary management of wounds includes an initial thorough cleansing of the affected area to remove any contaminants such as dirt, cloth particles, or other debris that may introduce pathogenic materials. Any hopelessly damaged tissues may be debrided and antiseptic materials are applied to make the area as sterile as possible. If considered necessary, sutures may be used to reduce the area of the underlying tissues and thereby limit the amount of tissue exposed to subsequent contamination.

The healing process is brought about by complex biological mechanisms generally involving several groups of special cells and proteins. Leukocytes, such as neutrophils and macrophages, crown the wound site and digest foreign pathogens and debris. Such cells also send out chemical signals that marshal fibroblasts in the wound vicinity and ultimately generate connective structures, principally, collagen, which make up a major portion of the new tissues. Endothelial cells generate new blood capillaries that grow into the reconstructed tissue areas where their presence is necessary to supply nutrients to the newly growing tissue cells and remove catabolic products. As the new capillaries grow, the cells on the margin of the wound simultaneously multiply and grow inwardly. The fibrous tissue arising from this cell growth eventually fills the wound cavity with a network of interlacing threads of collagen which in due time, arrange themselves in firm bands and form the permanent new tissue.

The surface of the wound is subsequently covered by processes of enlargement, flattening, and multiplication of the epithelial cells at the wounds' edge. These epithelial cells spread as sheets into the wound, beneath the scab. Eventually the proliferating epithelial cell sheets emanating from the wound sides coalesce to cover and close the wound on the outer surface. Until such time as at least superficial healing has occurred, or healing is impaired, the individual remains at risk from continued or new infection. Hence, there is a time versus rate related risk factor involved in all wound situations. The quicker the wound can heal, the sooner the risk is removed. Therefore, any procedure that can influence the rate of wound healing, or even favorably influence the healing of intractable wounds, would be of paramount value.

In accordance with this invention, improvements in the starch hydrolysate treatment of wounds have been developed to provide dressing for wound treatment, effective to promote the healing process, as well as beneficial compounding of the starch hydrolysate material.

SUMMARY OF THE INVENTION

This present invention relates to compositions, methods and procedures that improve the ability of wounds to heal and/or increase the rate at which wounds heal.

More specifically, the present invention presents compositions which, when applied to wounds, greatly enhance and promote the normal healing processes. Such compositions comprise suspension of a mixture of the fibrous protein, collagen type I; ascorbic acid; alpha-tocopherol acetate; and a starch hydrolysate.

In the process of the invention, the collagen type I/ascorbic acid/alpha-tocopherol/starch hydrolysate suspension is applied to the wound and maintained in contact therewith for an extended period, i.e., during the entire healing process, or until closure of the wound by new tissue has taken place.

The application of the collagen type I/ascorbic acid/alpha-tocopherol/starch hydrolysate suspension promotes the vascularization of the wound, attracts fibroblasts and endothelial cells by chemotaxis, and generally provides a favorable environment for the cells that participate in the healing process.

It is therefore an object of the invention to provide compositions that promote the tissue healing process.

It is another object of the invention to provide a method for promoting the healing of skin tissues.

It is further another object of the invention to provide collagen type I/ascorbic acid/alpha-tocopherol/starch hydrolysate compositions that promote skin tissue healing.

It is yet another object of the invention to induce improved rates of skin tissue repair by contacting wounds with a gel suspension of collagen type I/ascorbic acid/alpha-tocopherol/starch hydrolysate.

It is still another object of the invention to induce the healing of previously intractable wound.

It is yet another object of the invention to disinfect the wound covered with collagen type I/ascorbic acid/alpha-tocopherol/starch hydrolysate suspension.

It is further another object of the invention to provide collagen type I ascorbic acid/alpha-tocopherol/starch hydrolysate compositions that reduce scarring and may yet normalizes blood coagulation during therapy.

Compounding the starch hydrolysate composition to contain alphaketoglutaric acid, in addition to ascorbic acid or ascorbate salt, can provide a component which appears to be essential for activation of the tissue enzyme, protocollagen hydroxylase for collagen formation.

Another objective of this invention is to provide collagen type I/ascorbic acid/alpha-tocopherollstarch hydrolysate compositions as an article that promotes wound healing; reduces scarring and may yet normalize blood coagulation during therapy.

Other objects and advantages of the invention will become apparent from the following detailed description and the claims appended hereto.

BRIEF DESCRIPTION OF THE DRAWINGS

Other objects, features, and advantages of the present invention will appear from the following description taken together with the following figures. The accompanying figures, which are incorporated in and constitute a part of the specification, illustrate the effectiveness of presently preferred embodiments of the invention and, together with the detailed description of the preferred embodiment given below, serve to explain the observed results from using the invention on skin wounds. In some of the charts, for brevity, Maltodextrin has been abbreviated as "Malt," collagen type I has been abbreviated as "Coll," and alpha-tocopherol (Vitamin E) has been abbreviated as "Toco".

DESCRIPTION OF THE PREFERRED EMBODIMENT

The present invention relates to compositions and procedures that improve the ability of skin wounds, e.g., second and third degree burns, stasis ulcers, trophic lesions such as decubitus ulcers, severe cuts and abrasions to heal and/or increase the rate at which wounds heal. The invention includes a method for treating burns and exudative lesions with a medicinal dressing. The suspension may be a powder, or a viscous material such as a gel, paste, dispersion, solution or syrup.

The aforementioned skin wounds are characterized by openings or gaps in the skin tissue. As the healing process progresses, these open wounds are gradually filled in by new cells that appear across the surface of the wound, so that by the time the healing process is complete, new skin tissue covers the former open area of the wound. Such cells are termed granulation cells and the healing mechanism is a granulation cell formation process. These granulation cells are, however, very fragile and rupture easily. Heretofore, conventional dry gauze dressings have been used widely on such burns or exudative lesions. When dry gauze is removed, as for example when it is changed, the cells rupture; thus temporarily arresting the healing process. A dressing for burns and exudative lesions, therefore, should be capable of removal without disturbing the growth of the very fragile granulation cells.

As a defense mechanism the body rushes edema fluids to the area of these skin wounds and such wounds usually exude this edema liquid. Consequently, vital body fluids are lost in the exudate. If the loss of such fluids is great enough, shock ensues. Heretofore, the conventional technique to prevent this loss of vital body fluids has been to attempt to seal off the exuding wound. This has been accomplished, for example, by applying to the wound a layer of petrolatum or other water immiscible gelatinous hydrocarbon material. However, it has been found that the tissue under such a layer of petrolatum is often excessively soft and wet. This softened tissue causes difficulty in both autograft and homograft skin transplants. It also provides an environment that is conducive to the growth of secondary infections. The wound, therefore, must be cleansed constantly. But cleansing necessitates removal and replacement of the dressing and, as described above, there is great danger of rupturing the very fragile granulation cells during this removal and replacement process.

Gelatinous protein films have been used instead of a petrolatum seal in the treatment of burns or exudative lesions, but encounter the same problem of the underlying tissues becoming excessively soft. In addition, these films have a tendency to lift up and must then be removed and reapplied. This removal and replacement process again creates the possibility of rupturing the very fragile granulation cells.

A method for treatment of the aforementioned skin wounds, should therefore, employ a dressing that is as close as functionally possible to a natural wound scab. It should be permeable to exudate but not to proteinaceous material; be flexible and not lift up, and inhibit the start of spread of secondary infections by reducing the bacteria count around the treated wound. In the treatment of second and third degree burns, the dressing employed should be similar to a skin autograft in that it affords a natural protective covering which promotes healing, and yet it should, like a homograft, be easily sloughed off by the body when the healing process is completed.

The present invention provides a new and novel method of treating skin wound that comprises applying to the wound a sterile, purified starch hydrolysate material having a DE of less than about 35. DE is an abbreviation for "Dextrose Equivalent," which is an expression in the art for describing the total reducing sugar content of a material calculated as dextrose, and expressed as percent, dry basis. This value may be measured by any of the methods known in the art such as by the Luft-Schoorl Method (NBS Circular C-440), page 195 as appearing the "Polarimetry, Saccharimetry and the Sugars". A low DE starch hydrolysate product is one having a DE of less than about 35. As heretofore has been mentioned, in practicing the invention we use a sterile, purified starch hydrolysate material having a DE of less than about 35, however, the preferred sterile, purified starch hydrolysate materials have a DE of between about 5 and about 25. This material is water soluble, so that it need not be mechanically removed from a wound; it can be washed away by flooding with water. When applied to an exudative skin wound as a dressing, this material dissolves slightly in the exudate to form a covering that is very similar to a natural wound scab. This covering has been found to be somewhat flexible so that some movement of the treated area is possible without causing the covering to lift up and away from the exudative wound.

The dressing also has been found to act as a semi-permeable membrane which allows edema liquids to pass through it while proteinaceous materials are retained within the body. The exudate is clean and relatively free of proteinaceous materials. It, therefore, does not support biological oxidation to the same extent as exude containing proteinaceous fluids is minimized while at the same time excessive build up of edema liquids is also minimized. The possibility of the patient going into shock is, therefore, greatly reduced.

When applied to an exudative skin wound, this dressing greatly reduced the bacterial count of an infected wound, and inhibits infection of an uninfected wound. Thus, the possibility of a secondary infection occurring is greatly reduced. Toward this end, the sterile, purified starch hydrolysate particulate material having a DE less than about 35 may be admixed with any of the antibacterial agents known to the art to be effective in the prevention, and/or treatment of secondary infections, e.g., iodine, penicillin, nitrofuranes and the sulfa drugs such as silver sulfadiazine. In addition, proteolytic enzymes known by the art to be effective in promoting healing may also be admixed with this particulate material. Furthermore, collagen type I, nutritive agents, such as amino acids, cystine and cysteine, vitamins such as ascorbic acid (vitamin C) and alpha-tocopherol (vitamin E), and particulate starch hydrolysate may also be admixed or applied on wounds to promote the formation and growth of healthy granulation tissue.

The sterile, purified starch hydrolysate material having a DE of less than about 35 can be applied as a particulate material such as a powder, or as a viscous material such as a gel, paste, dispersion, solution or syrup. Such viscous starch hydrolysate can be made by adding it to a non-toxic, polar liquid vehicle or carrier such as water, glycerin, glycol or polyol.

The low DE, sterile, purified starch hydrolysate material may be applied directly to the wound or to facilitate handling and storing, it may be applied to a bibulous backing as, for example, a sterile gauze pad. The bibulous backing can then be applied to the wound so that the starch hydrolysate material comes into direct contact with the wound. To promote the formation of this protective film, the treated wound should not be tightly bandaged, but should only be loosely covered so that the wound can "breathe." It has been found that application of this material serves also to reduce the pain that is usually associated with burns, ulcers, and the like. This film also has the aforementioned properties of being flexible, semi-permeable, soluble in water and anti-septic to the bacteria of the wound.

Starch hydrolysate materials for use in practicing the present invention are those having a DE of less than about 35, and preferably from about 5 to 25. These materials are produced from starch by hydrolysis. Starch is a polymer or anhydro D-glucose unit. Hydrolysis of starch produces a mixture of polymers of various molecular weights ranging from 200 glucose units or more down to maltose (2 glucose units) and D-glucose itself. Because of their nature, the accepted way to describe the polymers formed by hydrolysis of starch is by their DE value, which is an expression of the average extent of hydrolysis. Low DE products suitable for use in the present invention, can be made by subjecting the gelatinized starch to the hydrolytic action of an acid, or an enzyme and/or successive treatments with such agents. The hydrolysate so formed is then purified by conventional means such as by subjecting it to filtration, centrifugation, decantation or the like to separate and remove any water insoluble materials remaining after hydrolysis. This material, dissolved in water to the extent of 10 grams per 100 ml will contain less than 0.1 percent insoluble materials as determined by filtration and drying the residue to constant weight under vacuum at 100° C. If desired the hydrolysate material may be subjected to further purification steps known to the art such as carbon or clay treatment, dialysis, electro-dialysis, osmosis, ion exclusion, ion exchange and the like. The starch hydrolysate material employed in practicing the invention may by prepared from starch by a number of specific methods.

Suitable starch hydrolysate materials may also be made via a number of other routes. For example, a mixture of starch and water having a solid content less than 50 percent may be first subjected to the hydrolytic action of a bacterial alpha-amylase. After an initial thinning by the enzyme, the resulting partial hydrolysate is heated to a temperature sufficient to solubilize any unsolubilized starch. Since this temperature also tends to inactivate the enzyme, it is then necessary to subject the solubilized partial hydrolysate to a second hydrolysis by treatment with more bacterial alpha-amylase to obtain the final starch hydrolysate. Another method of making the preferred class of starch hydrolysate materials consists of hydrolyzing mixtures of starch and water by the action of acid to reach a DE of less than about 35. The partial hydrolysate is subsequently subjected to the action of bacterial alpha-amylase to obtain a starch hydrolysate having a DE between 5 and 25.

A particularly preferred product useful here has the following specifications: moisture content of 5 percent maximum; 9–13 DE: pH of 4.5 to 5.5 which in aqueous solution at 10 percent solids; an average bulk density of 28–35 pounds per cubic foot and a descriptive ratio of about 2.

Any starch or starch like material may be used to prepare the starch hydrolysate material used in the invention. Suitable materials include cereal and tuber-starches, such as corn, wheat, potato, tapioca, rice, sago and grain sorghum, waxy starches may also be used. Hydrolysis may be carried out by enzymes, acids or in combinations of the two. The materials used in practicing the invention should, of course, be sterile. Sterilization may be accomplished by any of the known sterilization procedures.

For the purpose of illustrating the present invention but not of limiting the same, there are set forth below several examples of the novel methods of treatment and medicinal dressings herein described. As noted, besides the aqueous phase, there are three important components in the compositions. The use of free-radical scavengers as anti-inflammatory drugs is discussed in the *Handbook of Inflammation*, Volume 5: The Pharmacology of Inflammation pages 255–281 (Elsevier Science Publishers BV, 1985). Superoxide anion serve an indispensable purpose in the killing of phagocytosed microorganisms. Superoxide anion and reaction products such as hydroxyl radical are said to be deleterious in the extracelluar environment, possibly leading to self-maintenance of the inflammatory reaction and to tissue damage. The authors report the successful treatment of a variety of inflammatory conditions by injection of the enzyme superoxide dismutase (SOD), which catalyses the reaction:

$$2O_2^- + 2H^+ \rightarrow O_2 + H_2O_2$$

The authors point out a number of difficulties in the concept of scavenging free radicals by drugs rather than by enzymes. In particular, the reaction of free radical and scavenger generates a new free radical. If this is as reactive as the original radical, no benefit has been obtained. If it is less reactive, it may migrate away from the wound site and cause damage in a previously healthy area. The authors conclude that scavenging of highly reactive radicals in vivo is neither feasible nor desirable.

Chemical groups that are precursors for persistent free radicals contain no unpaired electrons. They are capable of reacting with active free radicals to produce persistent free radicals. Polymers that carry such precursor groups are generally preferred to those that initially carry persistent free radicals, for a number of reasons. There are a wide variety of such groups, and they are generally chemically stable and easy to prepare. Suitably chosen groups can engage in more than one free radical reaction, whereas persistent free radicals can in general engage in no more than one. In such a case, the precursor group reacts with an active free radical to form a persistent free radical, which subsequently quenches a second active free radical. Such precursor groups may engage in more than one free radical reaction in a variety of ways, depending on the chemistry of the substances involved.

U.S. Pat. No. 5,667,501 describes compositions which a polymer $p^1$ scavenges an active-free radical R. to form a persistent free radical ($P^1R$), which subsequently quenches another active free radical R. by addition. Polymers applied as wound dressings and remote from the wound on a molecular scale, are able to affect the wound healing process apparently through their ability to react with free radicals from the site of biological activity in the wound.

Low concentrations of hydrogen peroxide (around $10^8$–$10^6$ M) have been shown to stimulate fibroblast proliferation. This is particularly desirable during the later stages of wound healing. Polymers that carry groups that are precursors of free radicals are often capable of reacting with molecular oxygen in a physiological environment to generate hydrogen peroxide. The process is catalyzed by iron ions present at physiological concentrations.

It has been found that Vitamin C rescues vitamin E radical and regenerates vitamin E not only in homogeneous solution but also in liposomal membrane system. The efficiency or relative importance of vitamin C with vitamin E radical interaction is smaller in liposomal membrane system than in homogeneous solution. This is because vitamin C suppresses the consumption of vitamin E almost completely in homogeneous solution, whereas vitamin E is consumed appreciably even in the presence of vitamin C during the oxidation of liposomal membranes initiated with lipid-soluble radical initiator. The lipid peroxyl radicals in the membrane must be scavenged exclusively by vitamin E. The vitamin E radical formed may undergo several competing reactions. It may scavenge another peroxyl radical to give stable product, react with another vitamin E radical to give a dimer, or interact with vitamin C to regenerate vitamin E. The lower the peroxyl radical concentration, the higher is the efficiency of vitamin E regeneration. Apparently, this efficiency depends also on the accessibility of vitamin C to the vitamin E radical in the membrane.

The close proximity of the chromanol head group to the membrane surface is consistent with the synergistic antioxidant behavior of vitamins C and E observed in peroxidations of artificial phospholipid membranes using lipid-soluble, thermal azo initiators. Although the two vitamins are completely sequestered and separated in their respective liquid and aqueous phases, a very significant extension of inhibition of peroxidation is obtained when both are present. Vitamin C by itself is a good antioxidant when peroxyl radicals are generated in the aqueous phase, but it is very much less effective when radicals are generated within a membrane. Presumably, vitamin C can not penetrate the membrane sufficiently to interact with a peroxyl radical present there. The most likely explanation of the synergy between vitamins C and E is that vitamin C is able to reduce the tocopheroxyl radical back to alpha-tocopherol. The chemical feasibility of this regeneration mechanism has been amply demonstrated in homogenous media. A decrease of vitamin C at the site of injury will decrease the rate of wound healing.

Vitamins C and E function as water-soluble and lipid-soluble chain-breaking antioxidants, respectively, and protect lipids, proteins, and membranes from oxidative damage. Vitamin C scavenges oxygen radicals in the aqueous phase, whereas vitamin E scavenges oxygen radicals within the membranes. Vitamin C regenerates vitamin E by reducing vitamin E radicals formed when vitamin E scavenges the oxygen radicals. This interaction between vitamin C and vitamin E radicals can take place not only in homogeneous solutions, but also in liposomal membrane systems where vitamins C and E reside separately outside and within the membranes respectively, and vitamin C can act as a synergist.

The effect of vitamin E on wound healing is complex. Vitamin E can be secured from Sigma Chemical Company (St. Louis, Mo.) as alpha-tocopherol acetate preparation in oil that does not oxidize in air. It has been determined that vitamin E should be present in the aqueous dispersion at an optimal concentration of about 8–10 $\mu$g/ml. The relative concentration of the vitamin E component must be maintained within fairly well defined limits. If the concentration of vitamin E is too high, there is inhibitory effects or inflammatory reactions. The preferred concentration of vitamin E in this invention is 10 $\mu$g/ml.

Another function of these antioxidants, vitamins C and E is their chemotactic factors. Studies with patients in serious trauma indicate that the observed neutrophil locomotory dysfunction is partly due to auto-oxidation as shown by evidence of pre-activation of diminished reducing capacity and low serum and cellular levels of vitamin C and vitamin E. To investigate whether replacement of the antioxidant vitamins C and E, could improve the neutrophil locomotory defect, vitamin C, vitamin E, vitamin C and vitamin E, or placebo was administered to a total of 46 victims of blunt trauma. Locomotion data analyzed at 2–6 days after injury were compared. Compared with placebo, the antioxidants improved neutrophil locomotion. The mean differences in distance migrated (treated minus placebo) were vitamin C and vitamin E=11.3±3.0 $\mu$m (p=0.001) (mean±SE); vitamin C=4.7±3.4 $\mu$m (p=0.19); and vitamin E=3.3±2.9 $\mu$m (p=0.27). Although both antioxidants given together produced the best results, a plot of the 95% confidence intervals indicated that vitamins C and E, either given alone, were also better than placebo. Hence, they concluded that antioxidant replacement therapy significantly improved the neutrophil locomotory abnormality in blunt trauma.

In this invention, chemotaxis of vitamin C was tested both in vitro and in vivo. Chemotaxis can be determined by several means. Tests can be run in Boyden chambers according to the techniques taught by Boyden in Journal of Experimental Medicine Vol. 115, p. 453 et seq. (1962). The Boyden Chamber was used as follows: A suspension of neutrophils was obtained by injecting sterile mineral oil into the peritoneal cavity of young, healthy guinea pigs. At the end of several days, the peritoneal fluid containing neutrophils was harvested and preserved for in vitro testing in the Boyden Chamber. This solution was placed in the upper chamber of the Boyden Chamber and the various potential chemo-attractants were placed in the lower chamber. The chemo-attractants used are listed in the Table shown, and the number of neutrophils chemoattracted is also listed. The Maltodextrin, NF is the starch hydrolysate materials for use in practicing the present invention having a DE of less than about 35, and preferably from about 5 to 25 containing 1% vitamin C.

TABLE 1

IN VITRO CHEMOTACTIC ACTIVITY OF MALTODEXTRIN, NF ON POLYMORPHONUCLEAR LEUKOCYTE (BOYDEN CHAMBER).

| Material Tested | Average # Cells/Field |
|---|---|
| RPMI - 1640 | 4 |
| N-fmet - leu-phe | 60 |
| 10% Maltodextrin, NF | 9 |
| 30% Maltodextrin, NF | 185 |
| Sucrose | 5 |
| Chemokinesis Control | 10 |

In vitro tests using the Boyden Chamber showed that a 30% Maltodextrin solution attracted 185 neutrophils/field whereas N-finet-leu-phe, a strong chemo-attractant pulled only 60 cells/field. Serial biopsies from patients with Stage III and Stage IV pressure ulcers treated with Normal Saline dressings (Control) or Maltodextrin were obtained and the histology compared. In the Maltodextrin treated ulcers, granulation tissue was actively formed. The size and number of capillaries was greater. The capillaries were engorged with neutrophils actively migrating into the well-hydrated interstitial tissue, which contained large number of neutrophils and dividing fibroblasts. In the saline treated ulcers, the capillaries were smaller and fewer. Neutrophils within the capillaries and interstitial tissue were far less numerous. The interstitial issue was fibrotic with inactive fibroblasts.

The demonstration of in-vivo chemotaxis in humans can be shown by anatomy pathological techniques. These techniques, which include several types of biopsies, show clearly and distinctly large number of leukocytes including neutrophils, lymphocytes, monocytes and macrophages responding to chemo-attractive Maltodextrin; also fibroblasts and endothelial cells are chemoattracted towards areas where the Maltodextrin dressing is placed during the course of clinical wound/ulcer treatments. The observed healing effect of Maltodextrin is believed to be due in part to its chemotactic effect that produce growth factors known to promote healing. The formed film is a biological dressing that enhances the body's own cells to carry out the task of granulation. The data indicates that Maltodextrin may be efficacious in enhancing the healing of pressure ulcers and that 30% Maltodextrin for eight weeks is the most effective regimen tested. Statistical significance ($p<0.05$) was observed for chemotactic activity of Maltodextrin, NF on PMN leukocytes group and control.

The wound treatment can include ascorbic acid in admixture or application along with the starch hydrolysate material to promote the formation and growth of healthy granulation tissue. Ascorbate salts such as those of sodium, potassium and calcium can also be employed, though ascorbic acid is the preferred component for blending with the starch hydrolysate powder at a level in the range of approximately 0.5–20 weight percent of the blended composition. Preferably about 5–7.5 weight percent corresponding to a weight ratio of approximately 20 parts starch hydrolysate to one part ascorbic acid or ascorbate salt. While ascorbic acid appears somewhat more effective than the ascorbate salts and is less readily oxidized mixtures of ascorbic acid and ascorbate salt can also be employed in order to reduce acidity. Generally, in the preparation of wounds for treatment with starch hydrolysate dressing, the patient selected for study is carefully examined, test areas photographed, and when possible the volume of the lesion measured. Biopsy, planimetric, bacterial culture, and sensitivity studies are made and thereafter the ulcer or wound is carefully, surgically debrided with all necrotic tissue removed mechanically. Enzymatic debridment can also be carried out when necessary, usually employing proteolytic enzymes such as Travase, Biozyme, collagenase, and Elase. When the lesions are grossly infected or contaminated, treatment for a few days (one up to 3–4 days) with topical antibacterial agents, can be employed particularly when Gram-Negative organisms are present, such as *Pseudomonas aeruginosa* and *E. coli*; suitable agents include silver nitrate (0.1%–0.5%) solution and Silver-Sulfadiazine cream (Silvadane®, Sulfamylon®).

Broadly, the treatment procedure in accordance with this invention begins with irrigation of the wound, typically employing a syringe for pressure irrigation. Thereafter, the wound is covered with the starch hydrolysate composition preferably containing both ascorbic acid and alpha-ketoglutaric acid. The initial application of the starch hydrolysate material should be sufficient in amount to allow formation of a film over the entire area of the wound. A perforated non-adhering dressing (of the Dermnanet™ type) can be applied over the treated wound to allow removal of the dressing for daily repeating the foregoing treatment. Preferably, further irrigation of the wound is carried out by slight moisturization of the Dermanet™ dressing with a minimal amount of amino acid solution as described hereinafter. A roller bandage may then be applied.

Another important component in this composition is collagen. Collagen has many properties when put in contact with a wound bed. These properties include a homeostatic effect, interaction with platelets, interaction with fibronectin, increase in fluid exude, increase in cellular component, increase in growth factors and support for fibroblastic and eventually epidermal proliferation. Collagen plays a significant role in all phases of wound healing. Collagen lays out a matrix upon which skin grows and maintains its integrity. Wound healing has several distinct phases:

inflammation: platelet aggregation, cell recruitment;
granulation tissue formation: neovascularization; and
extracellular matrix deposition: wound contraction.

Components of the extracellular matrix, including collagen, are involved in every stage of wound healing. The first event, immediately following injury, is blood vessel disruption leading to extraversion of blood constituents, followed by platelet aggregation and blood coagulation. Collagen has a key role in these processes. It is analogous to the wrought iron or steel infrastructure, which shapes and provides structural integrity to a high-rise building. When a building is damaged, the first step is to replace the infrastructure. Other finishing building materials cannot be applied until the infrastructure is in place. Hemostasis or stoppage of bleeding is the first step of any wound healing process. Blood platelets and soluble clotting factors are the major intravascular hemostatic factors. Exposed collagen in the wound function to promote platelet aggregation following vascular injury. Collagen is a very efficient hemostatic agent because platelets adhere to collagen, swell and release substances, which initiate hemostasis. Collagen can provide the positive and negative active polar sites as well as a molecule of sufficient size for platelet aggregation. Aggregating platelet release a large number of cytokines including platelet-derived growth factor (PDGF), a potent mitogen, and transforming growth factor Beta (TGF-β), a potent stimulator of extracellular matrix synthesis. Platelets also release a number of other molecules including fibrin, fibronectin and thrombospondin which further blood coagulation and are chemotactic for inflammatory cells. Neutrophils, the first cells recruited into the wound site, are responsible for removing bacteria from the area by releasing a large arsenal of proteolytic enzymes. Many of these enzymes are also capable of degrading components of the extracellular matrix. Collagen is frequently described as a stable, relatively inert component of the extracellular matrix. While this statement may be true of the collagen deposited and cross-linked into an extracellular matrix, the primary role of which is to provide an extracelluar framework or scaffold to support cells; collagen has been increasingly considered to be dynamic proteins involved in many cellular and developmental processes. Distinct roles have been elucidated for collagen during morphogenesis and development, platelet adhesion and aggregation, cell attachment, cell migration, angiogenesis and filtration in basement membranes. Contemporary techniques to assess collagen turnover have also indicated that collagen metabolism is much more rapid than once considered.

Collagen is a proteinaceous material comprising the major fibrous element of the mammalian skin, bone, tendon, cartilage, blood vessels, and teeth. Its biological purpose is to hold cells together in discrete units; and secondarily it has a directive role in developing tissues. The collagen proteins are distinctive in their physical characteristics in that they form insoluble fibers possessing high tensile strength. It is the fibrous nature of the collagen that serves to hold the various body structures and components together. While the basic molecular structure of collagen may be modified to meet the needs of particular tissues, all collagen are organized into a common structure consisting of three polypeptide chains that form a triple stranded helix. The triple stranded helical units, in turn, are formed into a quarter-staggered array of linearly aligned bundles that make up collagen fibers. The collagen fibers are stabilized by covalent cross-inks.

It has been shown that purified collagen can be utilized medically in reconstruction and cosmetic surgery for the replacement of bony structures or gaps in bony structures, and for filling out tissues where wrinkles have forms. In such usage, collagen is secured from mammalian sources, e.g., calves, whereby extraneous proteinaceous material is removed by various dissolution, precipitation and filtration techniques to leave a pure collagenous product. Mammalian collagen accelerates healing by increasing the concentration of cellular and noncellular elements, including fibroblasts and growth factors. Collagen has many properties when put in, contact with a wound bed. These properties include a homeostatic effect, interaction with platelets, interaction with fibronectin, increase in fluid exude, increase in cellular component, increase in growth factors and support for fibroblastic and eventually epidermal proliferation.

Unfortunately this pure natural collagen may induce antigenic response in the host subject. Such antigenic response in the host may be generated by the end portions of the collagen fibrils that are not helically bound. Fortunately these end portions of collagen can be cleaved therefrom by treatment with a proteolytic enzyme, e.g. pepsin. After digestion with pepsin, the cleaved peptide ends are discarded and only the central collagen bundles (tropocollagen) remain. These central collagen bundles have greatly reduced antigenicity and they can be used for the purposes noted above without undue antigenic side effects. Although reduced antigenic collagen is preferred, non-cleaved collagen that has been isolated from animal sources may also be used. It is only necessary that the collagen be prepared in a sterile condition in an aqueous suspension. Some inclusion of materials commonly associated with the collagen, e.g., polysaccharides, can be tolerated and do not interfere with the benefits of the wound healing compositions. Other forms of processed collagen are also useful in the compositions.

Collagen is the most abundant protein in the body. There are about eighteen types of collagen, each containing three polypeptides of about 1,000 residues per chain. The main function of collagen is to maintain the shape and to resist the deformation of the tissues. In a similar fashion, the ropelike collagen fibrils help to enhance bond strength and to resist deformation in the tissue bonding or sealing composition of the present invention.

Another advantage of collagen is that when collagen is heated it can be denatured, and solubilized for easy application as a gelatin-like solution. When cooled, the collagen is partially renatured, resulting in a gel formation with excellent tensile strength. Heated collagen, therefore, is an ideal protein component in the present tissue bonding or sealing composition. Through heating, collagen can be solubilized and easily injected or applied, and by cooling it can be turned into a gel which provides both tensile strength and flexibility to the bond. Collagen can also be rendered in a sterile form. Moreover, collagen is more stable than its fibrin counterpart, both on the shelf and in vitro and collagen does not expose the recipient to the risk of contacting infection as does fibrin glue.

Properly configured bovine collagen, which preserves collagen's molecular structure, is dramatically different from products, which utilize a perverted form of the collagen molecule. The difference is analogous to the difference between particleboard and wood. Both are made of the same raw materials; however, with particleboard the integrity of the raw material is compromised and then reconstituted using a foreign substance. This results in dramatically different composition and effectiveness of the product. Changing the molecular structure of the product results in an even more profound difference. A molecule which does not maintain its basic properties essentially becomes a different molecule. It is similar to separating hydrogen and hydroxide molecules which comprise water. The separation leaves you with some useful chemistry, but certainly not something you drink.

Collagen type I can be found in most tissues and organs, but is most plentiful in dermis, tendon, and bone. Type I collagen is a 300 ηm-long heterotrimer composed of two alpha ($\alpha_1$) (I) chains and one $\alpha_2$(I) chain. Collagen-binding integrin receptors are $\alpha_1\beta_1$, $\alpha_2\beta1$, and $\alpha_3\beta_1$. In the present invention collagen type I from human placenta is preferred in the concentration of 0.2–2 $\mu g/cm^2$ in the aqueous dispersion. It is commercially available from Becton Dickinson Labware, Bedford, Mass. The material has been tested and found not reactive for hepatitis B surface antigen (HBsAg), for antibody to hepatitis C virus (anti-HCV), for antibody to human immunodeficiency virus-1 (anti-HIV-1) and for antibody to human immunodeficiency virus-2 (anti-HIV-2). It has also been tested and found negative for the presence of bacteria, fungi, and mycoplasma The purity is tested by electrophoretic homogeneous (SDS-PAGE). It is effective as a gel or thin coating at the recommended concentration. The collagen should be present in the aqueous dispersion at an optimal concentration of about 0.2–2.0 $\mu g/cm^2$. Considerable variation above or below the noted concentrations is permissible so long as undue inflammation does not occur. It is desirable to hold the concentrations close to the stated amounts to produce optimum results, and to avoid inhibitory effects or inflammatory reactions. The preferred concentration for collagen is 2.0 $\mu g/cm^2$.

For the purpose of illustrating the present invention but not of limiting the same there is set forth below several examples of the novel method and compositions of the present invention for wound treatment and medicinal dressings herein described.

EXAMPLE 1

The subject for this example was a 78 year old man afflicted with Buerger's disease, or arteritis obliterans, that was manifested by chronic, foul smelling, seeping deep ulcerations of both legs. The subject was undernourished and previous attempts to treat the ulcers, by several standard methods, had failed. The ulcers were of a third degree depth, and extended along most of the length of the anterior aspect of the legs. The lesions on the right leg were selected for treatment with a sterile, purified starch hydrolysate particulate material. The lesions on the left leg were treated, as a control, impregnated with nitrofurazone gauze, a widely used treatment for bums and ulcerated lesions. Bacteriological cultures were taken at various intervals from the lesions of both legs. The treated lesions were inspected every other day.

Immediately, the starch hydrolysate material in powdered particulate was dusted, in a thin film, onto the ulcer bed or granulation tissue of the lesions upon the subject's right leg, it was wetted by the serum exudate present at the ulcer site and shortly this wetted hydrolysate product dried up and formed a pliable, thin film. Over this newly formed film a plain, gauze dressing was placed. As compared to the lesions treated with the gauze impregnated with nitroflurazone, there was a definite decrease in the amount of fluid exuded from the lesion treated with the starch hydrolysate product. In addition, there was a decrease in the odor of the test site, and a decrease in the pain. The color of the exudate formed at the starch hydrolysate treated site was of a light brown, caramel nature, as compared with the control site, which was a dark, ugly greenish-blue.

A few days after the initial application of the starch hydrolysate product, a change in the characteristics of the granulation tissue of the treated lesion was observed. This granulation tissue became progressively cleaner and bright red, beginning to grow, or fill up, towards the surface of the leg. The gauze over the treated site became securely attached to the wound, whereas the gauze over the control remained unattached. The gauze at the treated site, could be loosened by washing with water, when inspection or changing of the film was desired. As indicated, the areas were inspected every other day. It was found that the epithelium began to grow in the ulcer that was treated with the starch hydrolysate product, both from the perimeter of the lesion and from the depth of the lesion. After 7 weeks, the test lesion had completely healed, or filled with newly formed epithelium. This new skin was flexible, warn and pink. The control site, however, after this 7-week period, evidenced no decrease of infection, or exudation nor any growth of epithelium. In fact, the control treated ulcerated lesion deepened to the point of involving the muscles of the subject's leg, which became necrotic. Bacterial cultures taken during the course of the treatment became negative in the starch hydrolysate dressing. However, bacterial infection persisted almost unabated in the control or nitrofurazone treated lesion.

EXAMPLE 2

The subject was a 13 year-old girl with a third degree burn of the dorsal aspect of the right foot. The burn was thermal in nature, being caused by boiling water. The subject was treated with antibiotics. At the end of 14 days of treatment, separation of the eschar took place, leaving a deep area of granulation tissue. This area was treated, in the conventional manner, with nitrofurazone impregnated gauze. After a period of three weeks of treatment, the condition of the burn site remained unchanged and, in fact, became progressively more infected. At this point, as no growth of epithelium was observed, normally a split thickness skin auto-graft would have been applied in order to effect healing of the burn.

Instead, however, starch hydrolysate material of this invention in a powdered, particulate form, was applied every other day, to the burn site. After the formation of the thin film, as described above in Example 1, the burn site was covered with a layer of dry gauze bandage. As with Example 1, the following observations were made: there was a decrease in pain from the moment of the application of the hydrolysate product; a decrease of the infection at the burn site; an improvement in the quality and appearance of the granulation tissue, and a progressive growth of the epithelium from the periphery to the center of the burn site. After 5 weeks, the burn site was completely covered by newly formed epithelium, without any appreciable contracture. After 4 months, no contracture of scars was observed in the area of the original burn site.

EXAMPLE 3

The subject, a woman 51 years old, was affected with bilateral deep stasis ulcers of both legs, at the lower third of the leg. The right leg ulcer was rather small, and measured approximately 3 by 4 inches. The ulcer on the left leg, in contrast, covered completely around the leg in a circular fashion, and had a width of 5 inches.

The drainage from both ulcers was considerable, the subject having to use several thickness of cotton dressing to control the drainage. The right leg ulcer was used as a control and treated, as in the examples above with nitrofurazone impregnated gauze. The left leg was dusted with the starch hydrolysate material of this invention, in powdered, particulate form every other day. After approximately 2 months, the leg treated with the starch hydrolysate product was almost completely covered by newly formed skin, with the exception of a centrally located area, which continued to decrease in size as new epithelium formed. As in the examples above, the following observations were made: there was a decrease of pain; a decrease of drainage and exudate; growth of granulation tissue; centripetal growth of the skin; and diminution of the bacterial flora and bacterial count. Again, as in the above examples, the nitrofurazone treated ulcer showed little healing.

EXAMPLE 4

The subject for this example was a 56 year-old woman who had had a deep stasis varicose ulcer on her right leg (internal lower aspect) for approximately 20 years. The wound measured 6 inches by 4 inches and had foul smell with an abundant yellowish-greenish purulent exudate. It was infected with abundant bacterial colonies of at least three species. Previous attempts to autograft and homograft over the area had been unsuccessful. The affected area was treated over several months with various available systemic and topical antibiotics with no change whatsoever in the status of the ulcerated area.

To this ulcerated area sterile, purified starch hydrolysate material in powdered particulate form was applied in an amount sufficient to form a thin layer over the wound. The DE of this material was about 9.9. Within a few minutes after application, the particulate material nmixed with the exudate serum to form a film. If left uncovered, the film wound dry up within an hour to form a solid, yet flexible covering over the ulcer site. This covering resemble a natural wound scab, and like a natural wound scab it prevents body fluids (i.e., plasma) from escaping and regulates temperature exchanges from the body through the wound.

Following applications of the particulate material at intervals of 2 or 3 days, it was noticed that the exudate from the wound diminished appreciably so that after fifteen days of such treatment of the ulcer site showed no evidence of purulent exudate or other debris. After this time the centripetal growth inside the wound site was estimated to be about 2½ inches with the ulcer reduced to 1½ inches×¾ inch in size. With a magnifying glass the advancing edge of the epidermis could be seen growing into the granulation tissue covering the reduced site of the ulcer. There was no pain associated with the treatment.

EXAMPLE 5

The subject was an 11 year old girl who had suffered first and second degree thermal burns (scalding water) on the left flank of her abdominal wall (her left side above the hip area). The burn site was 7 inches by 4 inches. To this burn area sterile, purified starch hydrolysate material in powdered, particulate form was applied in an amount sufficient to form a thin layer over the burn. The DE of this material was about 9.9. On the second post-burn day the superficial layers came off having second degree burn. After daily treatment with the particulate material for 6 days, the burn area was fully re-epithialized. There was no infection and no pain associated with the treatment.

EXAMPLE 6

The subject was a 5 year-old girl who had second degree thermal burn (hot coffee) on her forearm. The burn was 3 inches by 1 inch and had three small areas of third degree burn. The burn was treated as in Example 5 with sterile, purified starch hydrolysate material in powdered, particulate form on the third post-burn day. At that time the burn was already infected. The DE of the material used was about 9.9. The material was applied every other day. After 10 days the burn area was fully healed and covered by new epithelium including the third burn areas. One month later there was no evidence of scarring.

EXAMPLE 7

Based on these previous excellent results that were obtained as demonstrated above on enhancing wound healing, further trials were conducted on animals using the Maltodextrin/collagen/alpha-tocopherol combinations. These studies focused on a comparison of results between Maltodextrin alone, Maltodextrin plus collagen type I, Maltodextrin plus alpha-tocopherol, and Maltodextrin plus collagen plus alpha-tocopherol on wound healing and explored its mechanism of action on the proliferation of keratinocytes (epidermal layer) and fibroblasts (dermal layer) in vivo. This was done by:

A) Assessing the rate of wound healing by Maltodextrin and its various combinations on mature CD-1 male mice. This was also accomplished by:
  I) Measurement of wound areas by planimetry technique as described by Danon et al., 1989.
    i.) Healing was expressed as a percentage of the original wound area healed.
B) Assessing the biologic activities of Maltodextrin and its various combinations on mature CD-1 male mice. This was accomplished by:
  I) Histomorphometric analysis of the healing tissue by light microscopy and patterns of DNA synthesis by 5-bromo-2'-deoxy-uridine (BrdU) incorporation into cellular DNA, since oxygen radicals impede healing by causing damage to DNA, cellular membranes, proteins, and lipids. This was accomplished by:
    i) Immunocyto-/immunohistochemical evaluation of proliferating DNA synthesis in the epidermis and dermal layers of the skin tissue.

In this test 60 mature (8 to 10 week-old) male CD-1 mice (Charles River, Wilmington, Mass.) were used for the test. The wounding technique described by Danon et al. (1989) was used with minor modifications. In brief, the mice were anesthetized, and their backs shaved with hair clippers. Twelve animals were randomly assigned in each of the experimental group. Two full-thickness cutaneous wounds were made on each mouse by punching one hole on the back with a 6-mm sterile biopsy punch (Acuderm Inc., Ft. Lauderdale, Fla.). Each mouse in each of the 5 groups received either of the topical application of:

Group 1: Control (saline); Group 2: 50 mg Maltodextrin; Group 3: 50 mg Maltodextrin plus 2 $\mu g/cm^2$ collagen Type I; Group 4: 50 mg Maltodextrin plus 10 $\mu g/ml$ alpha-tocopherol; or Group 5: 50 mg Maltodextrin plus 2 $\mu g/cm^2$ collagen Type I plus 10 $\mu/ml$ alpha-tocopherol, daily for 10 days. All wounds were allowed to heal without occlusive dressings. Wound areas were measured by planimetry as previously described (Danon et al. 1989). Healing was expressed as the percentage of the original wound area that was healed. The results were presented as means ±SEM. The statistical significance was determined by Student's t-test. P-values of <0.05 were considered significant.

On Day 10, 1 ml of the BrdU per 100 g body weight of the animal was injected intraperitoneal approximately 3–4 hours prior to sacrificing the animals. The healed tissue was harvested from the sacrificed animals and processed for immunocyto-/histochemical evaluation of the proliferating DNA synthesis, using the BrdU Labeling. Blood was collected for serum chemistry to evaluate any increase in glucose. Kidneys were harvested for histology (Hematoxylin & Eosin stain) to rule out toxicity. BrdU (Boehringer Mannheim Corp., Indianapolis, Ind.) was used to label cells during DNA replication (DNA synthesis=S phase of cell cycle). Those cells that have incorporated BrdU into DNA are easily detected directly using a monoclonal antibody against BrdU conjugated with a reporter enzyme such as alkaline phosphatase (AP). This assay is an immunocyto-/histochemical technique that uses a mouse monoclonal antibody against BrdU conjugated with AP. After injecting BrdU into each animal to label the DNA in vivo, only proliferating cells incorporate BrdU into their DNA. The animals were sacrificed and skin tissues prepared for sections. The fixed BrdU-labeled tissue and the cellular DNA are denatured by acid (HCl) or heat (microwave method). The incorporated BrdU is detected using an AP-conjugated anti-BrdU monoclonal antibody, $F(ab')_2$ fragment (anti-BrdU-AP). The bound anti-BrdU-AP is visualized with the substrate Fast Red. AP converts the substrate to an insoluble colored compound, which precipitates at those sites of the immunocomplexes. The samples were then analyzed under light microscope.

Histomorphometric analysis of the healing tissue was pooled from 50 microscopic fields of each animal in the group for data collection.

Preparation of Maltodextrin, Collagen Type I, and Alpha-Tocopherol.

The compositions of the present invention are prepared from commercially available dispersions of the individual components. The Maltodextrin, NF used in this invention is manufactured by DeRoyal Industries, Inc. as described above containing 1% ascorbic acid. Collagen type I from human placenta as described above is a commercial product diluted with sterile normal saline to the concentration levels noted above, e.g., 2 $\mu g/cm^2$. Commercial alpha-tocopherol acetate solution is added with good mixing to the diluted collagen suspension to achieve the desired level, e.g., 10 $\mu g/ml$. The resultant colloidal suspension had a pH of 4.5 to 5.5 to match that of the Maltodextrin. For some purposes it may be desirable to thicken the compositions into a more viscous or semi-solid gelled state. If such is desired, standard medically acceptable gelling materials, e.g. cellulose, may be included in the compositions.

The prepared compositions should be maintained under refrigeration or maintained at room temperature. When kept under refrigeration, the suspensions will maintain their effectiveness for extended periods, i.e. months. Although the compositions may be used as the aqueous colloidal suspension of Maltodextrin, collagen type I, and alpha-tocopherol, per se, it is also possible to add small amounts of an antibiotic, e.g. neomycin sulfate, normally used for topical applications. Such addition of a topical antibiotic is not necessary to promote wound healing by the present compositions. Such addition is solely as a matter of convenience in the general management of wounds.

The wounds were first thoroughly cleansed and decontaminated as per standard medical practice and any necrotic tissue was debrided to leave as clean and sterile a wound surface as possible. A quantity of the saline-Maltodextrin-collagen type I-alpha-tocopherol was applied liberally to all surfaces of the wound with no occlusion over the wound. The wound healing composition was reapplied daily to the wound surfaces, and the wound was not covered with gauze dressings as noted above. This procedure was followed until new epithelial tissue completely closes the wound surface, at which time, application of the wound healing composition was discontinued.

Effects of Compositions on Wound Healing

Figure 1:
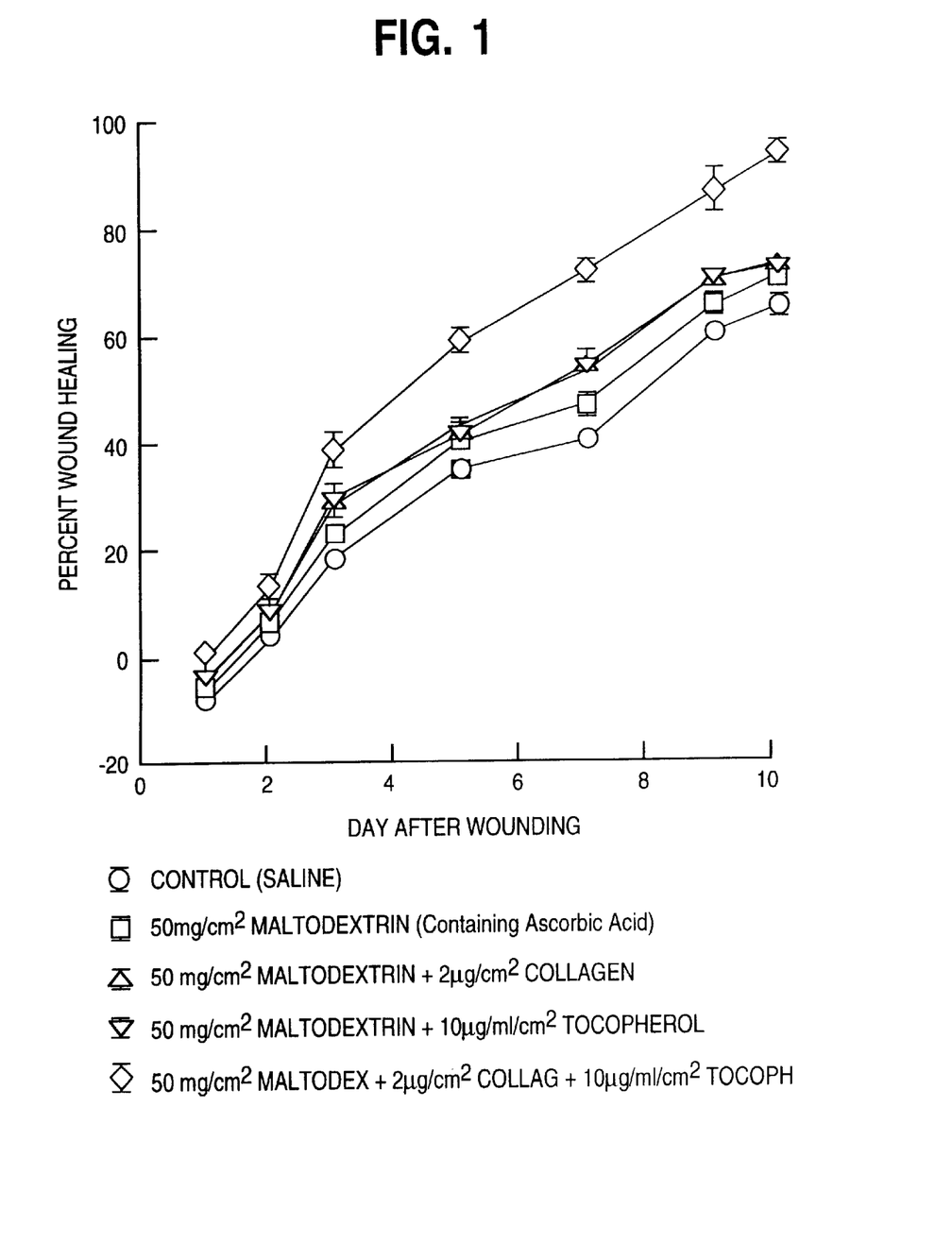
FIG. 1 is a graph showing the effect of the Maltodextrin, collagen type I, and alpha-tocopherol composition of the present invention on the healing a wound over time.

FIG. 1, demonstrates the effect of Maltodextrin, collagen type I, and alpha-tocopherol acetate on the healing of full-thickness wounds. The most unexpected significant improvement in the rate of wound healing was observed at the combination of Maltodextrin/collagen type I/alpha-tocopherol (97±2.3%, P<0.05) compared to Control, Maltodextrin alone, Maltodextrinicollagen type I or Maltodextrinialpha-tocopherol. Time cause and specificity studies indicated that this combination specifically and significantly promoted healing between 1 and 6 days after wounding as compared with control. Though the effects of Maltodextrin, Maltodextrin/collagen type I, or Maltodextrin/alpha-tocopherol were not statistically significantly (ANOVA, P>0.05) different from each other, they all showed significant (P<0.05) improvement as compared to the Control.

As noted previously, wound healing is a complex and involved process with features that include gross anatomy, microscopic processes, chemical change, cell migration, etc. The most direct and reliable method of gauging the wound repair process is histological examination. Such examination is, however, only semiquantitive. Nonetheless, histology does give a summation of all the complex process that take place during wound healing. Therefore it can be used to best assess the benefits derived from any procedures used to improve or hasten healing.

Figure 2:
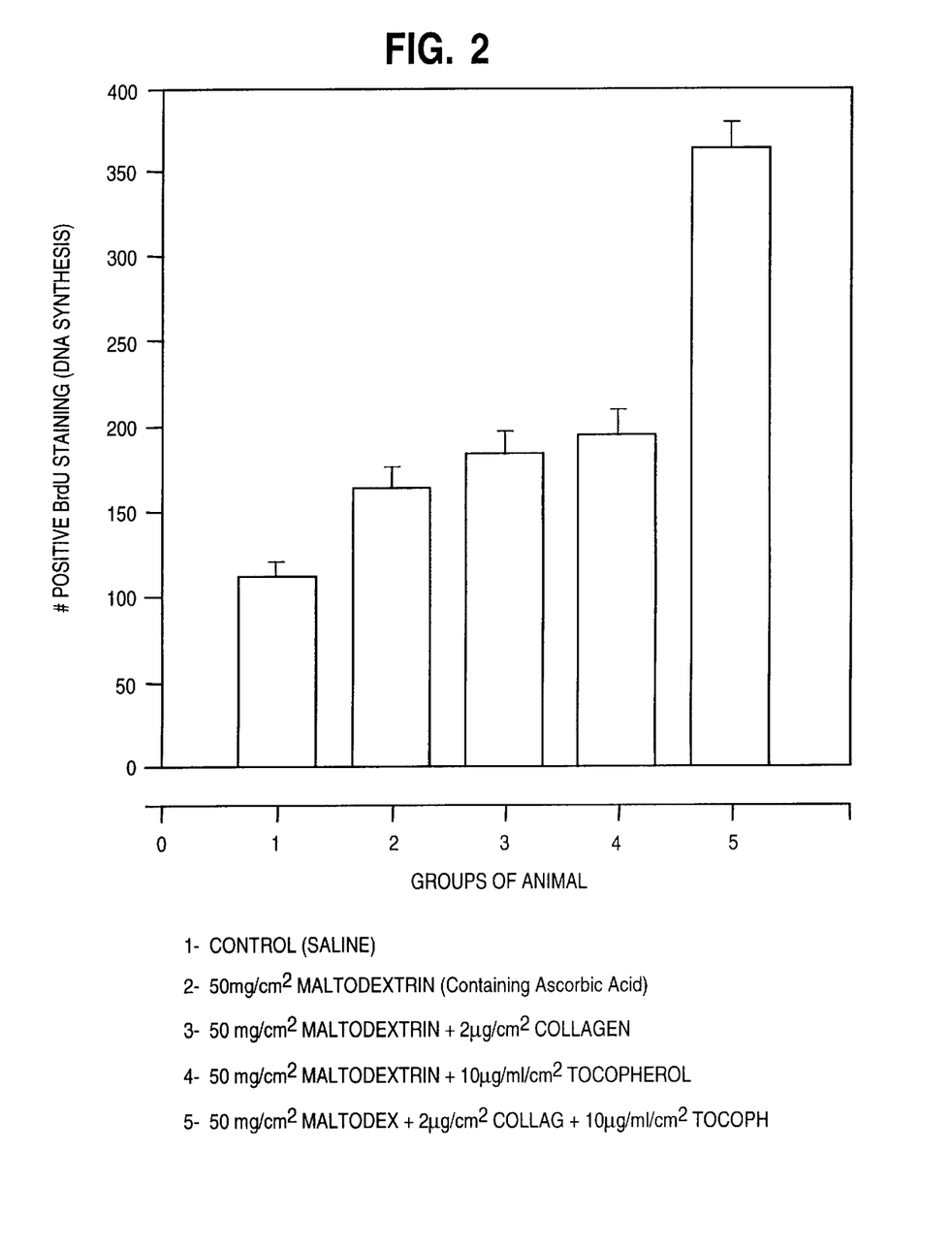
FIG. 2 is a chart showing the increase in the number of positively stained BrdU for various compositions, signifying DNA synthesis for each composition.

FIG. 2 demonstrates the number of positively stained BrdU signifying DNA synthesis among the groups. The staining confirmed that there was significant increase in the synthesis of DNA in the group that received Maltodextrinicollagen type I/alpha-tocopherol compared to the other groups.

Histological assessment of the wounds was made. The following are descriptive composites of the histological assessments: The wounds treated with Maltodextrinicollagen type I/alpha-tocopherol showed a cellular infiltrate extending through the wound to the base and consisted primarily of fibroblasts and monocytes. There were also new reticulin fibers, intense fibroplasia and rich network of new capillaries and venules in this group but not in the control wounds. The Maltodextrin, Maltodextrinicollagen type I, and Maltodextrin/alpha-tocopherol acetate treated groups, were closely similar histologically to the Maltodextrin/collagen type Italpha-tocopherol group, however, there was somewhat less vascularization. Histological examinations of the kidneys from all groups did not show any evidence of toxicity. Serum glucose levels were all within normal limits.

The influence of increasing concentration of alpha-tocopherol in the composition of Maltodextrin and collagen type I was tested. Based on the previous results that clearly demonstrated that Maltodextrinicollagen/alpha-tocopherol acetate accelerates wound healing, this study focused on the dose-response effect of alpha-tocopherol on wound healing. This was to determine the maximum therapeutic dose that will enhance and not inhibit wound healing or cause any irritation or toxicity to the animal and to assess the effect of scarring on the wounded animals with the topical application of the composition.

In this test, thirty (30) mature (6–8 week-old) female of the C57 BL/6 mouse (Charles River, Wilmington, Mass.) were used and fed a standard mouse chow diet ad libitum. The C57 BL/6 mouse was used because it has a highly synchronized hair cycle that can be easily evaluated as the hair cycle is the only location for the melanin production, and melanin is only produced during active hair growth. At the resting (telogen) stage, the color of the animal is pink; at the active or proliferative (anagen) stage, the color changes to dark gray marking an increase in pigmentation; and as the transition (collagen) stage, the color the animal is pinkish-gray. The materials and methods for evaluating the wound healing were as described above except for a few modifications. At the resting stage, the animals were anesthetized and their backs depilated with wax/rosin mixture as described by Paus et al, (1990). After 5 days, the animals were wounded as described above. The animals were randomized into 5 groups with 6 animals in each group. The wounds were dressed as described above daily with increasing doses of alpha-tocopherol in the Maltodextrin/collagen type I composition. The areas of wound healed were followed daily as in the previous experiment. After 8 days of dosing, the animals were sacrificed and their skin harvested for histological examinations just as described above.

Figure 3:
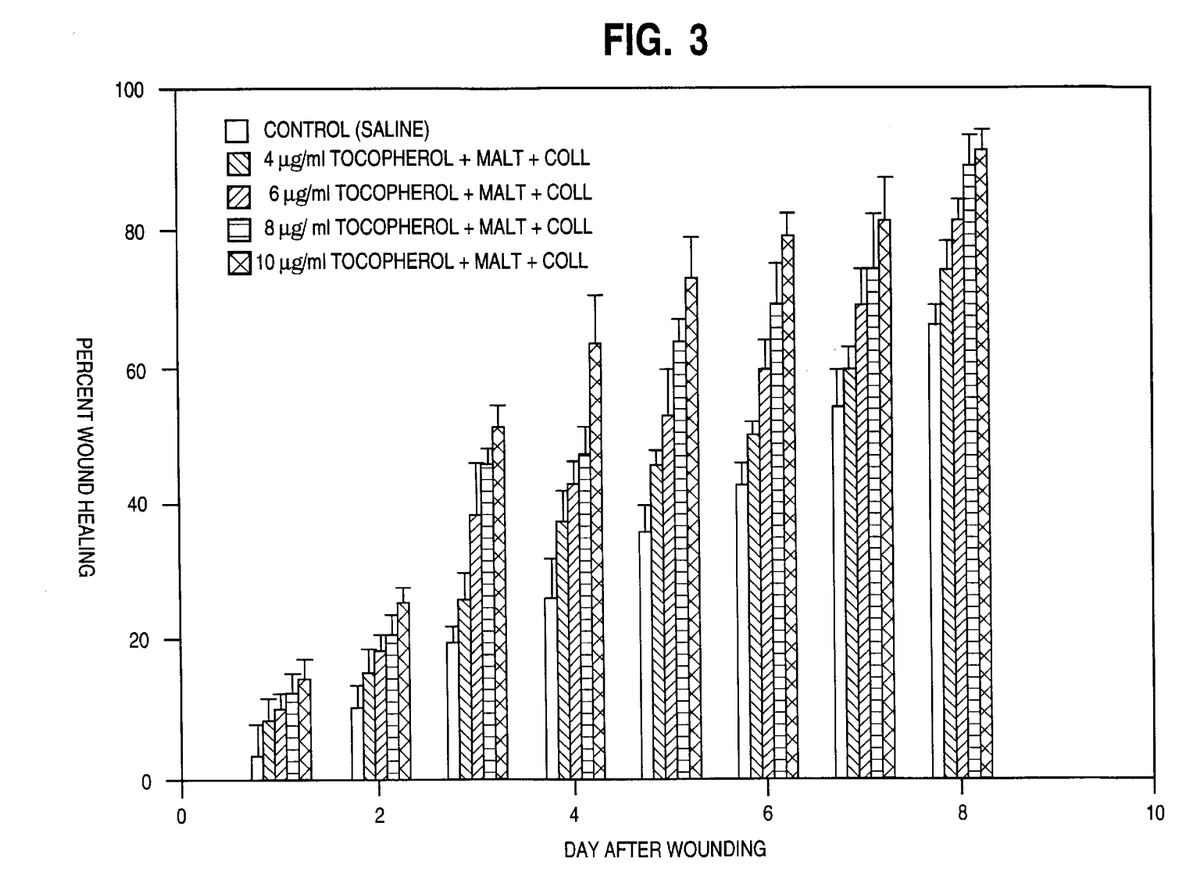
FIG. 3 is a chart showing a dose-dependent effect of alpha-tocopherol, the increase in the percentage of wound healing resulting from an increasing concentration of alpha-tocopherol in the compositions of the present invention on the healing of full-thickness wounds over time.

FIG. 3 demonstrates the effect of increasing concentration of alpha-tocopherol in the Maltodextrin/collagen type I composition on the healing of full-thickness wounds. There was, however, no significant increase or difference in the rate of wound healing between 8 and 10 $\mu$g/ml of alpha-tocopherol in Maltodextrin/collagen type I composition (90±4%, P<0.05). Though the effects of 8 $\mu$g/ml of alpha-tocopherol in the Maltodextrinicollagen type I was not statistically significantly (ANOVA, P>0.05) different from that of 10 $\mu$g/ml of alpha-tocopherol, it showed significant (P<0.05) improvement as compared to the other doses.

Figure 4:
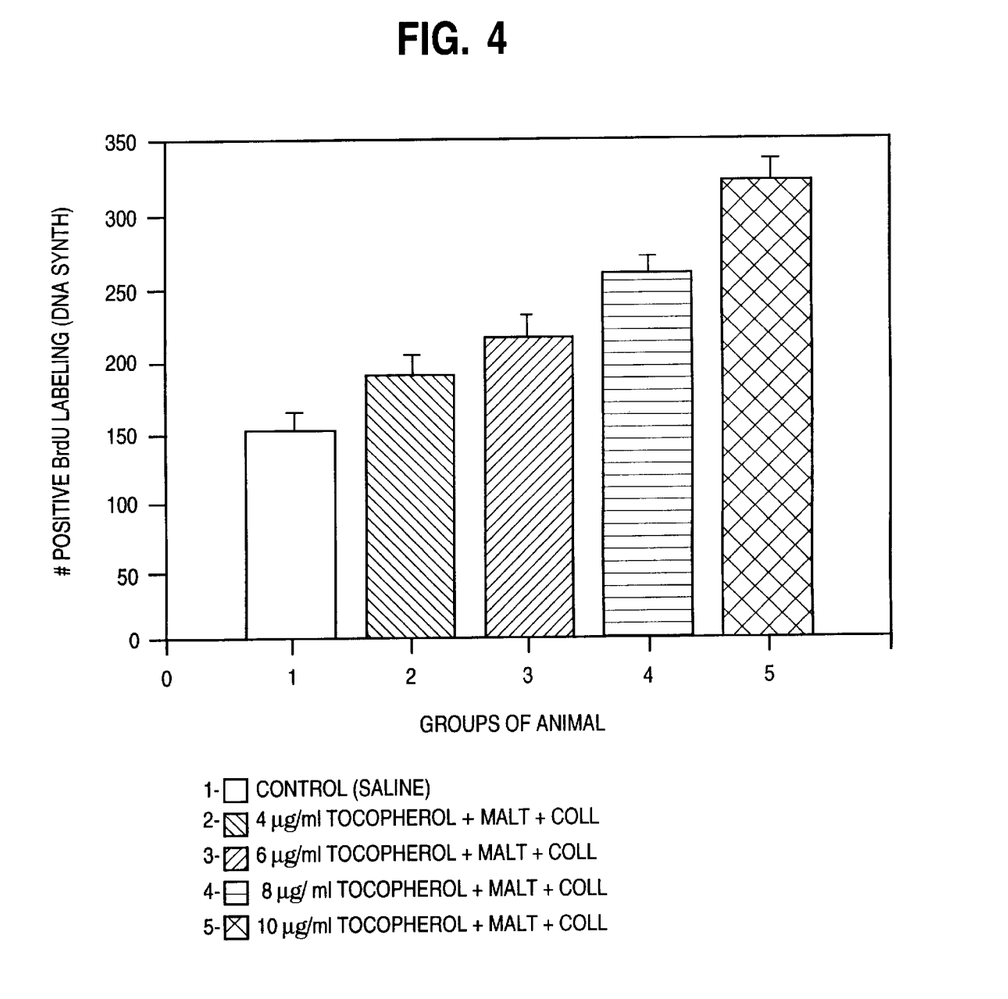
FIG. 4 is a chart showing the number of positively stained BrdU signifying DNA synthesis among various animal groups, confirming a significant increase in the synthesis of DNA correlating with the acceleration of wound healing in the Maltodextrin/collagen type I/alpha-tocopherol compositions of the present invention.

FIG. 4 demonstrates the number of positively stain ed BrdU signifying DNA synthesis among the groups. The staining confirmed that there was significant increase in the synthesis of DNA(P<0.05) in the acceleration of wound healing in the groups that received either 8 or 10 $\mu$g/ml of alpha-tocopherol compared to those that received either 4 or 6 Mg in combination of Maltodextrin and collagen type I. Macroscopic evaluations showed no irritation or scarring in these groups compared to the control. Histological examinations of the 8–10 $\mu$g/ml of the alpha-tocopherol in the composition were similar to those of group 5 above. Again, histological examinations of the kidneys from all groups revealed no abnormalities. The serum levels of glucose were also within normal limits. Therefore, it was found that the normal combination of collagen type I present on the order of 0.2–2 $\mu$g/cm$^2$; the 1% ascorbic acid in the Matodextrin, NF as prepared above and alpha-tocopherol present on the order of 8–10 $\mu$/ml in the comb ination, greatly accelerate the rate of wound healing and substantially reduces scarring.

While the foregoing few representative embodiments and details have been shown for the purpose of illustration and clearness of understanding, it will be apparent to those skilled in the art that various changes and modifications may be made in the treatment of surface wounds using a suspension of particles of collagen type I, ascorbic acid, and alpha-tocopherol with starch hydrolysate having a low DE of less than 35, which are chemotactic for fibroblasts and endothelial cells, dry suspensions, gel, aqueous suspensions, articles comprising combinations of the collagen, ascorbic acid, alpha-tocopherol with starch hydrolysate having a DE less than 35 as a suitable carrier selected from the group consisting of a gauze, sterile bandage or a tape therein without departing from the spirit or the scope of the invention. It is intended that all such changes and modifications will be embraced within this invention, provided they fall within the appended claims.

What is claimed is:

1. A method for promoting healing of a skin wound, comprising the steps of:
    applying to the wound a composition of a therapeutically effective aqueous suspension of bovine collagen type I and aipha-tocopherol in a mixture with starch hydrolysate having a low dextrose equivalent DE, wherein said composition is chemotactic for fibroblasts or endothelial cells.

2. The method of claim 1, wherein said bovine collagen is pre-treated to remove extraneous proteinaceous material by various dissolution, precipitation and filtration techniques to provide a pure collagenous product.

3. The method of claim 1, wherein said liquid aqueous suspension is applied repeatedly to the wound during the healing to effectively promote the healing process.

4. The method of claim 1, wherein a minor amount of ascorbic acid is combined in the suspension.

5. The method of claim 1, wherein two or more vitamins are combined in the suspension.

6. The method of claim 5, wherein the combined vitamins are vitamin C and vitamin E.

7. The method of claim 1, further including the step of adding vitamin C to the suspension in concentrations in the order of about 0.5–20 weight percent of the composition.

8. The method of claim 1, wherein concentration of vitamin E in the suspension is in the order of 8–10 $\mu$g/ml.

9. The method of claim 1, wherein the starch hydrolysate has DE of less than about 35.

10. The method of claim 1, wherein the starch hydrolysate has a DE between about 5 and about 25.

11. The method of claim 1, wherein the starch hydrolysate has a DE between about 9 and about 13.

12. The method of claim 1, wherein the suspension is gelled.

13. The method of claim 1, wherein the collagen is present in the suspension in concentrations in the order of about 0.2 to 2 $\mu$g/cm$^2$.

14. The method of claim 1, wherein the collagen is present in chemotactically effective amounts.

15. A method for promoting the healing of a skin wound, comprising the steps of:
    applying to the wound a composition of a therapeutically effective aqueous suspension of collagen in a mixture with starch hydrolysate having a low dextrose equivalent DE, wherein said composition is chemotactic for fibroblasts or endothelial cells.

16. The method of claim 15, wherein said collagen is derived from a mammalian source such as bovine.

17. The method of claim 16, wherein said bovine collagen is first treated to remove extraneous proteinaceous material by various dissolution, precipitation and filtration techniques to provide a pure collagenous product to effectively promote the healing process.

18. The method of claim 15, wherein alpha-tocopherol is combined in the suspension.

19. The method of claim 18, wherein a minor amount of ascorbic acid is combined in the suspension.

20. The method of claim 18, wherein vitamin C and vitamin E are combined in the suspension.

21. The method of claim 18, including the step of adding vitamin C to the suspension in concentrations in the order of about 0.5–20 weight percent of the composition.

22. The method of claim 20, wherein the concentration of vitamin E in the suspension is in the order of 8–10 $\mu$g/ml.

23. The method of claim 15, wherein the starch hydrolysate has DE of less than about 35.

24. The method of claim 15, wherein the starch hydrolysate has DE between about 5 and about 25.

25. The method of claim 15, wherein the starch hydrolysate has DE between about 9 and about 13.

26. The method of claim 15, wherein the suspension is gelled.

27. The method of claim 15, wherein the collagen is present in the suspension in concentrations in the order of about 0.2 to 2 $\mu$g/cm$^2$.

28. The method of claim 15, wherein the collagen is present in chemotactically effective amount.

29. A method of treating a skin wound which comprises the steps of applying to the wound an amount of starch hydrolysate having a DE of less than about 35 effective to form a film over said wound, the starch hydrolysate having a descriptive ratio of about 2.

30. A method for promoting healing of a surface wound, which method comprises applying to the wound a suspension including starch hydrolysate having a low dextrose equivalent DE, bovine collagen, alpha-tocopherol, and a minor amount of vitamin C, the collagen being chemotactic for fibroblasts or endothelial cells, wherein the suspension is applied repeatedly to the wound during the healing to effectively promote the healing process.

31. A composition for use in promoting healing of a surface wound, comprising an aqueous suspension of starch hydrolysate having a DE of less than 35, purified bovine collagen type I which has been treated to remove extraneous proteinaceous material, and alpha-tocopherol, wherein the amount of alpha-tocopherol is below that which produces an inhibition of migration of cells into a wound area, and is below that which produces undesirable local inflammation.

32. The composition of claim 31, wherein the suspension further comprises two or more vitamins in the pH range of 4.5 to 5.5.

33. The composition of claim 31, wherein the aqueous suspension is gelled.

34. A composition for use in promoting healing of a surface wound, comprising a liquid aqueous suspension of a bovine collagen type I in admixture with a starch hydrolysate with a DE of less than 35 that exhibits a chemotactic effect on fibroblasts or endothelial cells, wherein the collagen is purified from a human placenta, and the collagen is present in the suspension at a concentration of about 0.2 to 2 $\mu$g/cm$^2$.

35. A composition for use in promoting healing of a surface wound, comprising a liquid aqueous suspension of vitamin E and collagen type I, in admixture with a starch hydrolysate with a DE less than 35 that exhibits a chemotactic effect on fibroblasts or endothelial cells, wherein the collagen is in the suspension at a concentration of 2 $\mu$g/cm$^2$.

36. The composition of claim 35, further comprising a minor amount of ascorbic acid.

37. The composition of claim 35, wherein the vitamin E is present in the amount of about 8–10 $\mu$g/ml.

38. A composition for use in promoting healing of a surface wound, comprising agents that greatly accelerate the rate of wound healing and reduce scarring, comprising of a liquid aqueous suspension of collagen in the order of 0.2–2 $\mu$g/cm$^2$, Maltodextrin, NF as in admixture with a starch hydrolysate having a DE less than 35, and alpha-tocopherol in the order of 8–10 $\mu$g/ml in the suspension.

* * * * *